United States Patent [19]

Chareire

[11] Patent Number: 4,650,486
[45] Date of Patent: Mar. 17, 1987

[54] QUICK CONNECT SYSTEM FOR CONNECTING A BLOOD VESSEL AND A CARDIAC PROSTHESIS

[75] Inventor: Jean-Louis Chareire, Levallois, France

[73] Assignee: Societe Nationale Industrielle Aerospatiale, Paris, France

[21] Appl. No.: 667,170

[22] Filed: Nov. 1, 1984

[30] Foreign Application Priority Data

Nov. 9, 1983 [FR] France ................... 83 17807

[51] Int. Cl.⁴ ............................................. A61F 2/22
[52] U.S. Cl. .................................. 623/3; 128/334 C
[58] Field of Search ............. 128/334 R, 1 D, 334 C; 3/1.4; 623/3

[56] References Cited

U.S. PATENT DOCUMENTS 3,766,567 10/1973 Kahn et al. ...................... 3/1.7

Primary Examiner—Richard C. Pinkham
Assistant Examiner—Gary Jackson
Attorney, Agent, or Firm—Marshall, O'Toole, Gerstein, Murray & Bicknell

[57] ABSTRACT

A quick connect system for connecting a blood vessel and a cardiac prosthesis comprises two cooperating annular connectors, one fixed to the prosthesis and the other to the end of the blood vessel. A removable obturating plate is mounted on the connector fixed to the cardiac prosthesis so as to be able to slide in a plane at least substantially orthogonal to the axis of the connector, this plate comprising an outward extension enabling it to be gripped, when it is in its obturating position. The invention is particularly useful in heart surgery.

7 Claims, 10 Drawing Figures

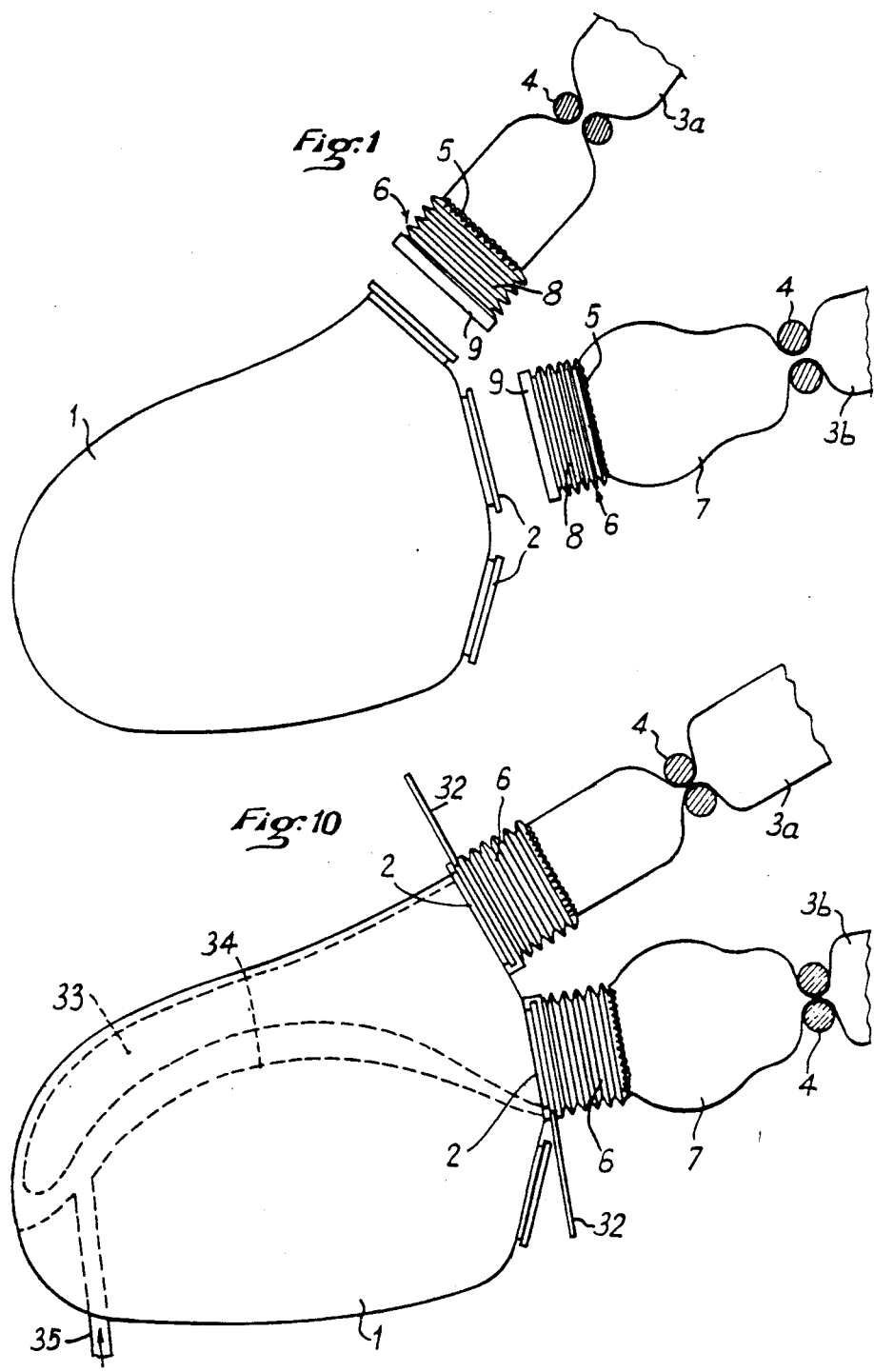

QUICK CONNECT SYSTEM FOR CONNECTING A BLOOD VESSEL AND A CARDIAC PROSTHESIS

The present invention relates to a quick connect system for connecting a blood vessel and a cardiac prosthesis, comprising two cooperating annular connectors, of which one is fixed to said prosthesis and the other to the end of said blood vessel.

The operation of grafting an artificial heart is known to be effected schematically in the following manner:
- the patient is connected to an extra-corporal blood circulation and the vessels arriving at or leaving the heart are temporarily obturated;
- the natural heart is cut out at the limit between the two atria and the two ventricles, as well as at the beginning of the aorta and the pulmonary artery;
- a quick connector is fixed by suture to the end of each of the two arteries and the two atria, the artificial heart being provided with corresponding connectors;
- the artificial heart is offered and the four quick connectors for connecting the vessels are positioned on those of the artificial heart;
- and the air is bled from the artificial heart and the atria and arteries, up to the extra-corporal circulation zone.

The air bleeding operation is at present the most difficult to carry out and represents more than half the time of the operation. Moreover, it is never certain that it has been carried out perfectly, which means that the patient runs a considerable risk: in fact, a very small quantity of air arriving at the brain can lead to death or to very serious, irreversible damage.

It is therefore a principal object of the invention to render the air bleeding operation quick and reliable and to provide a quick connection system to this end.

To this end, according to the invention, the quick connect system for connecting a blood vessel and a cardiac prosthesis, comprising two cooperating annular connectors, of which one is fixed to said prosthesis and the other to the end of said blood vessel, is characterized in that:
- a removable obturating plate is mounted on said connector fixed to the cardiac prosthesis so as to be able to slide in a plane at least substantially orthogonal to the axis of said connector, this plate comprising an outward extension enabling it to be gripped, when it is in its position of obturation;
- said connectors are provided with reciprocal connecting means enabling them to be joined one to the other, when said plate is in its position of obturation of said connector fixed to the cardiac prosthesis, without preventing the movement of slide of said plate; and
- said connector fixed to said blood vessel is provided with a seal which, when the connectors are joined one to the other, ensures tightness therebetween, and which locks said connectors in their position of connection, if said plate is separated by sliding from said connector which bears it.

Said obturating plate is advantageously transparent.

As will be seen in greater detail hereinafter, the structure of the quick connect system according to the invention:
- allows the artificial heart to be filled, just before the operation, with the patient's blood to which anticoagulant has been added;
- makes it possible to check that the heart is perfectly filled, thanks to the transparent obturating plates which show any air bubbles;
- allows fixation on the artificial heart of the four connectors connected to the blood vessels;
- facilitates bleeding of the volumes included between said connectors and the temporary obturations of the veins and arteries; and
- simultaneously allows communication of the blood volumes contained in the artificial heart and the connectors connected to the vessels up to the temporary obturations of the latter and the locking of the connectors on the heart, without take-up of air.

For each connect system, the removable obturating plate preferably moves parallel to a radial direction of said connector fixed to the cardiac prosthesis and said means for reciprocal connection of said connectors enable the latter to be joined one to the other by a movement of slide in a direction parallel to the radial direction of slide of said plate.

In an advantageous embodiment, the outer part of the connector fixed to the prosthesis forms a flange adapted to be held prisoner between a pair of coaxial, parallel rings borne by the connector fixed to said blood vessel and the ring of said pair located towards the outside is open in order to allow said connectors to be joined by sliding. The obturating plate is housed and guided in a flat recess made in the face of said flange directed outwardly, said recess opening out on the periphery of said flange.

The seal advantageously comprises a tubular part coaxial to said rings of the connector fixed to said blood vessel and an annular part at right angles to the axis of said tubular part, this annular part being disposed towards the inner face of the inner ring of said pair and being anchored on its periphery on said connector fixed to the vessel, whilst said tubular part passes in the central hole of said inner ring to project between said rings and, when the connectors are joined one to the other, the free end of said tubular part, on the one hand, is applied on said plate if the latter is in its position of obturation or in a position of partial obturation and, on the other hand, is applied on the bottom of said flat recess serving as housing for the plate by hooking behind the edge thereof, if said plate is separated from the connector which bears it.

The edge of said flat recess and the corresponding edge of said plate are preferably shaped as a dove-tail widening inwardly of the connector fixed to the cardiac prosthesis.

The invention will be more readily understood on reading the following description with reference to the accompanying drawings, in which:

FIG. 1 schematically illustrates an artificial heart and two blood vessels which are to be connected thereto.

FIG. 10 illustrates a process for connecting the prosthesis according to the invention.

Figure 3:
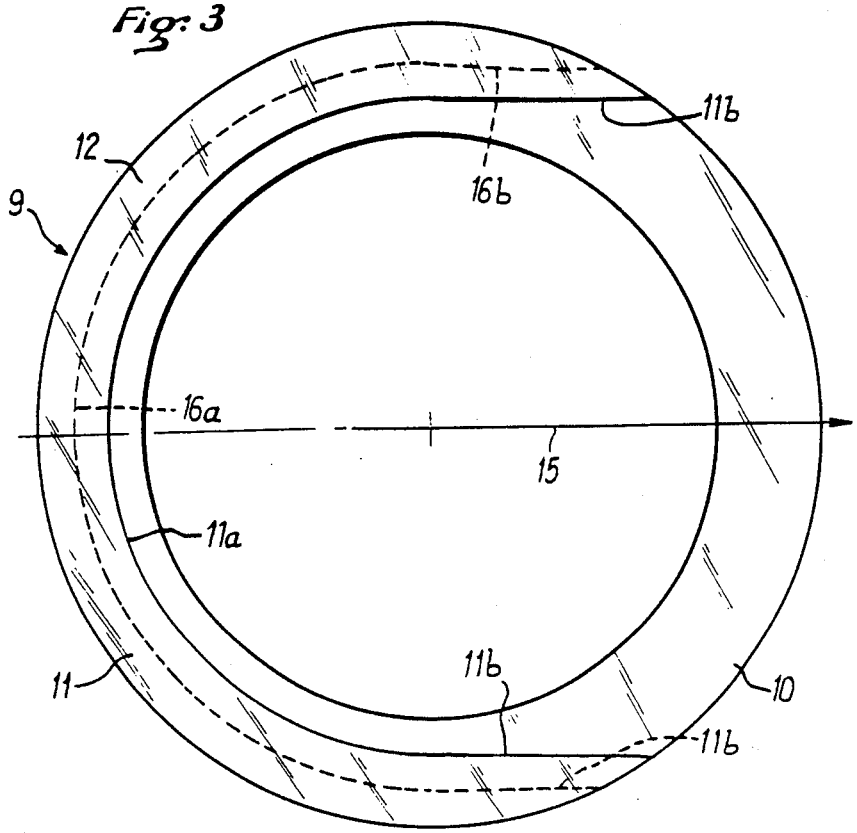
FIG. 3 is an end view, in the direction of arrow III of FIG. 2, of the connector shown therein.

In these Figures, like references designate like elements. FIGS. 2 to 9 are views of an embodiment of the invention, enlarged by about four times the normal size. In known manner, the connectors connected to the cardiac prosthesis comprise a valve not forming part of the present invention and of which the direction depends on whether said connector is intended for connecting a vein or an artery. Except for the direction of said valve, the system according to the invention shown in FIGS. 2 to 8 may be used both for connecting a vein and for connecting an artery.

Referring now to the drawings, FIG. 1 shows a cardiac prosthesis or artificial heart 1 provided with four connectors 2 (of which only three are visible) having to be connected to two arteries 3a, namely the aorta and the pulmonary artery (of which only one has been shown) and to two veins 3b, namely the vena cava and the pulmonary vein (of which only one has been shown).

For grafting the prosthesis 1, the surgeon connects the patient to an extra-corporal blood circulation system (not shown) and temporarily obturates the arteries 3a and veins 3b by means of clipping devices 4. He then cuts out the natural heart (not shown), for example at the limit between the two atria and the two ventricles, and at the beginning of the aorta and the pulmonary artery. He fixes, by sutures 5, the connectors 6 to the cut ends of the arteries 3a and the atria 7, these connectors 6 each being capable of cooperating with one of the connectors 2 of the heart 1 to form a quick connect system. Each of the connectors 6 comprises a tubular bellows 8, made of a haemo-compatible material such as DACRON (Registered Trademark), serving to connect it to the corresponding vessel 2 or 3 and a flange 9, for example made of titanium, serving to fix it on a connector 2.

Figure 2:
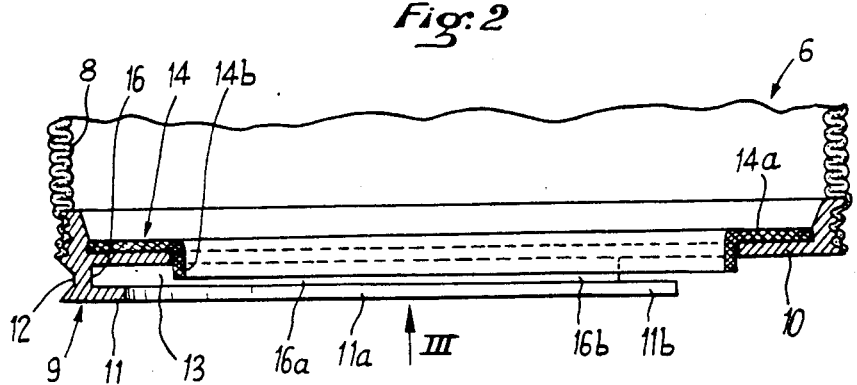
FIG. 2 shows, in axial section, a connector according to the invention, having to be fixed on a blood vessel to be connected to the artificial heart.

As shown in FIGS. 2 and 3, the flange 9 is constituted by two parallel, coaxial, flat rings 10 and 11, fast with each other on their periphery by a rim 12 and spaced apart to form therebetween a flat space 13, in the form of a disc having a diameter greater than the inner diameters of said rings. The bellows 8 is fast with the flange 9 via the rim 12.

The inner ring 10, disposed on the bellows 8 side, presents an inner diameter smaller than that of the outer ring 11. An elastic seal 14, for example made of DEL-RAIN (Registered Trademark), coaxial to the rings 10 and 11, comprises an annular part 14a which is applied on the face of the ring 10 directed towards the bellows 8 and which is anchored by its outer periphery in the inner face of the rim 12, as well as a tubular part 14b, at right angles to said annular part 14a, and coaxial to rings 10 and 11, projecting inside said space 13 in the direction of the outer ring 11. The outer face of the tubular part 14b substantially follows the contour of the inner recess of the inner ring 10.

Furthermore, the outer ring 11 and the rim 12 are eliminated by machining over about half their periphery, so that the space 13 is open parallel to a radius 15 of the flange 9. This machining is effected so that the inner periphery of the outer ring 11 is constituted by a semi-circular part 11a, to which are connected two rectilinear parts 11b, parallel to radius 15. Similarly, the peripheral base 16 of the flat space 13 comprises a semi-circular part 16a, to which are connected two rectilinear parts 16b parallel to the radius 15.

Figure 4:
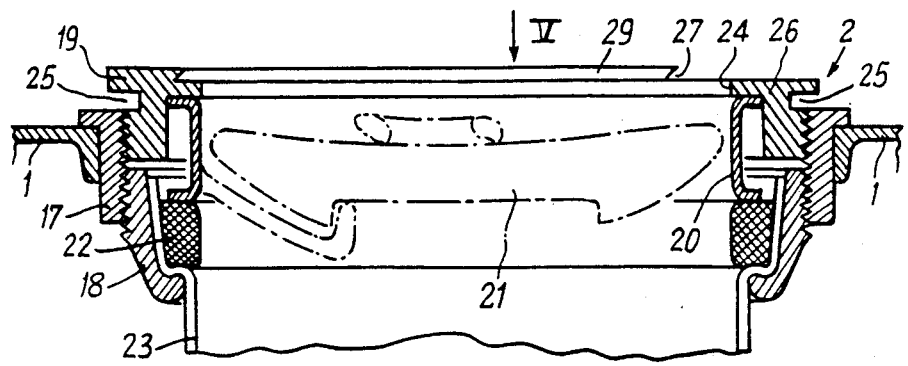
FIG. 4 shows, in axial section, a connector according to the invention, borne by the artificial heart.
Figure 5:
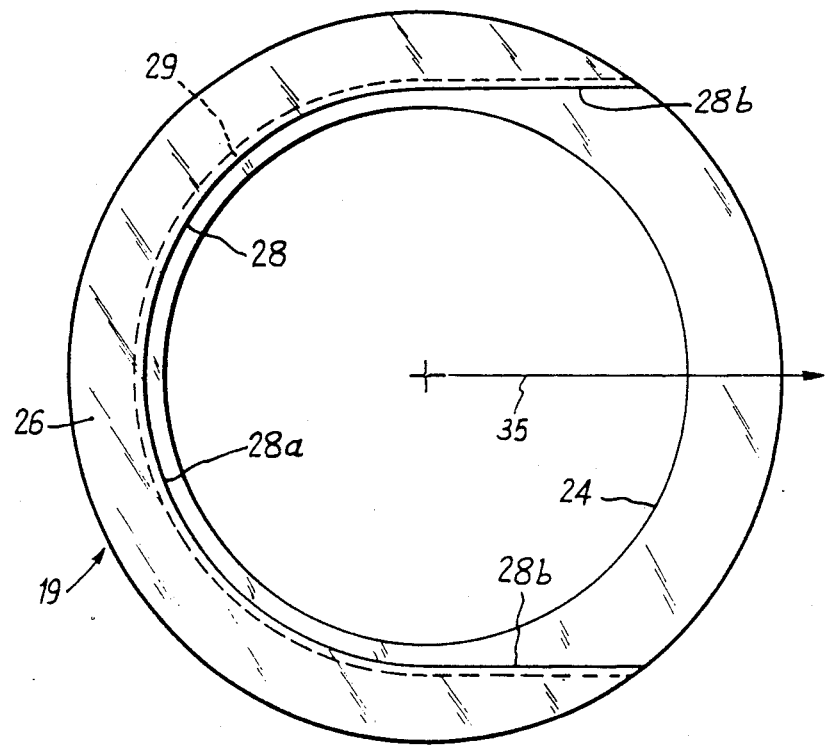
FIG. 5 is an end view, in the direction of arrow V of FIG. 4, of the connector shown therein.

As may be seen in FIGS. 4 and 5, a connector 2 comprises an annular ring 17, threaded internally and fast with the prosthesis 1. In the annular ring 17 are screwed, by their outer periphery, two rings 18 and 19, maintaining therebetween the cylindrical body 20 of the valve 21, mentioned hereinabove, as well as an elastic ring 22, serving to press a blood bag 23 constituting an active part of the prosthesis 1.

Ring 17, rings 18 and 19 and the body 20 may be made of titanium, whilst the elastic ring 22 and the blood bag 23 may be made of TEFLON (Registered Trademark) and polyurethane, respectively.

The outer part of the ring 19 is pierced with an inner hole 24 of which the diameter is at the most equal to the inner diameter of the tubular part 14b of the seal 14. A groove 25 is machined in the lateral wall of said ring 19 so as outwardly to define a flat ring 26:

The outer diameter and the thickness of the flat ring 26 are arranged to be slightly less than the diameter and the height of the disc-shaped space 13 of the connector 6;

The bottom diameter of the groove 25 is arranged to be slightly smaller than the inner diameter of the ring 11 of the connector 6;

The width of the groove 25 is arranged to be slightly larger than the thickness of the ring 11 of the connector 6.

In this way, the upper part of the ring 19 forms a sort of flange which may be fitted laterally in the flange 9 of the connector 6 by lateral slide through the opening of the ring 11. In fitted position of the two flanges 25, 26 and 9, i.e. in position of connection of connectors 2 and 6, as shown in FIGS. 6 to 9, the flat ring 26 is housed in the peripheral part of the space 13 and maintained by the rings 10 and 11.

Furthermore, in the upper face of the flat flange 26 is machined a flat recess 27 defined by an edge 28 formed by a semi-circle 28a of radius greater than that of the inner hole 24 of the ring 19 and at least equal to the outer radius of the tubular part 14b of the seal 14 and by two portions of straight lines 28b causing said recess to open out on the periphery of said flange 26. The edge 28 is shaped as a dove-tail 29 widening inwardly of the connector 2. In this way, the edge 28 may form a slide for a transparent plate 30, for example made of PLEXI-GLASS or LEXAN (Registered Trademarks), not shown in FIGS. 4 and 5, but visible in FIGS. 6 and 7. The movement of slide of the plate 30 is effected parallel to radius 35 of the ring 19 parallel to the portions of straight lines 28b.

The front edge of the plate 30 is defined by a dove-tail 31 cooperating with the dove-tail 29 of the edge 28. The plate 30 extends outside the connector 2 by an extension 32.

With a view to grafting the cardiac prosthesis according to the invention, said prosthesis is firstly filled with blood and the different connectors 2 are obturated by means of said plates 30. It will be noted that, due to the transparency thereof, it is easy to ensure that such filling is complete and that no air bubble is present inside the prosthesis.

Figure 6:
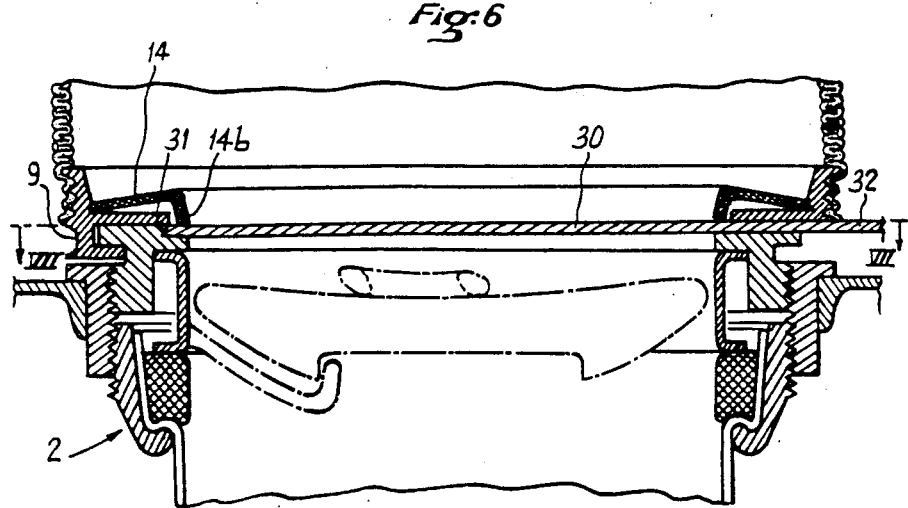
FIG. 6 illustrates the joining of the connectors of FIGS. 2 and 4, the obturating plate of the connector borne by the artificial heart being in position.
Figure 7:
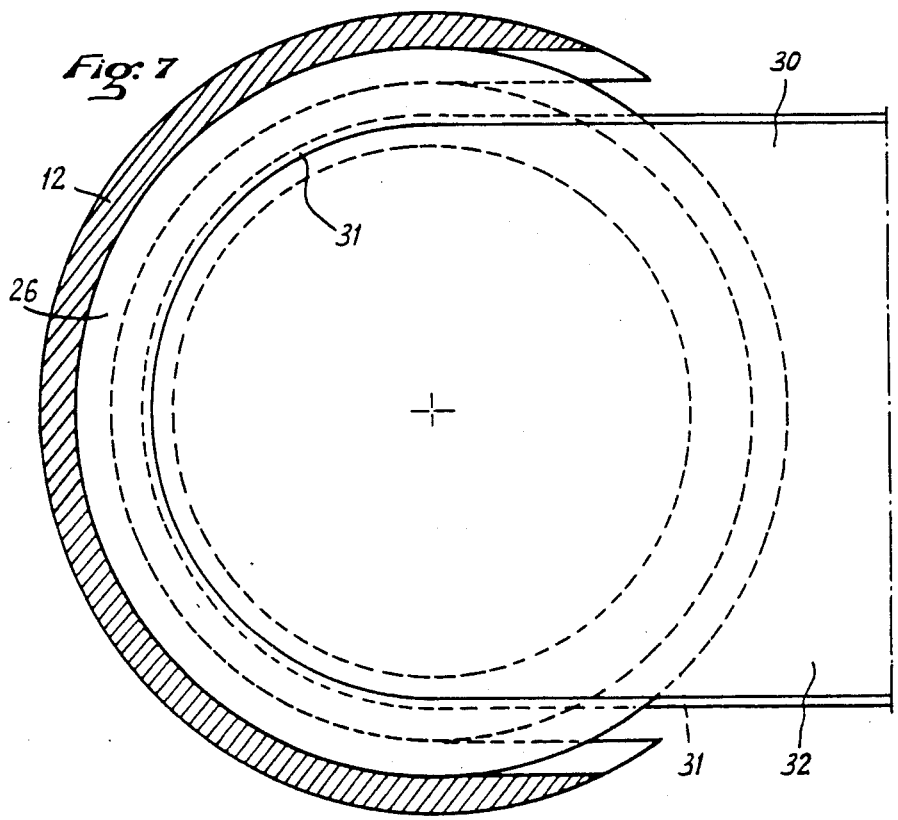
FIG. 7 is a section along the plane VII—VII of FIG. 6.
Figure 8:
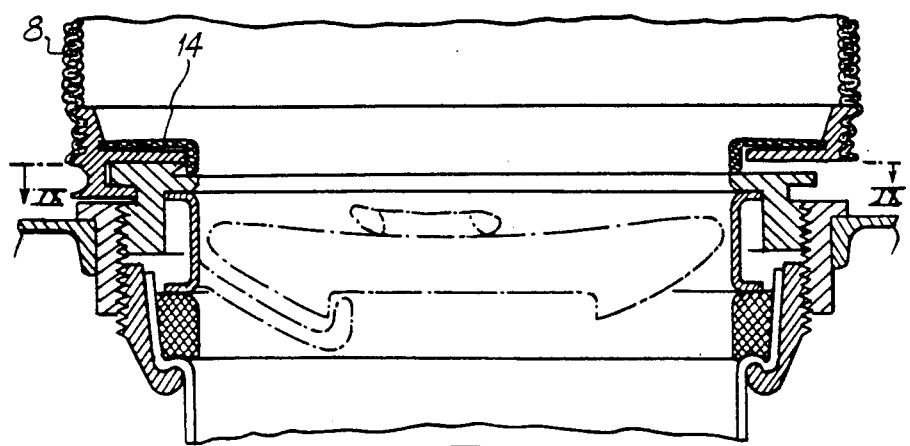
FIG. 8 illustrates the joining of the connectors of FIGS. 2 and 4, the obturating plate of the connector borne by the artificial heart being eliminated.
Figure 9:
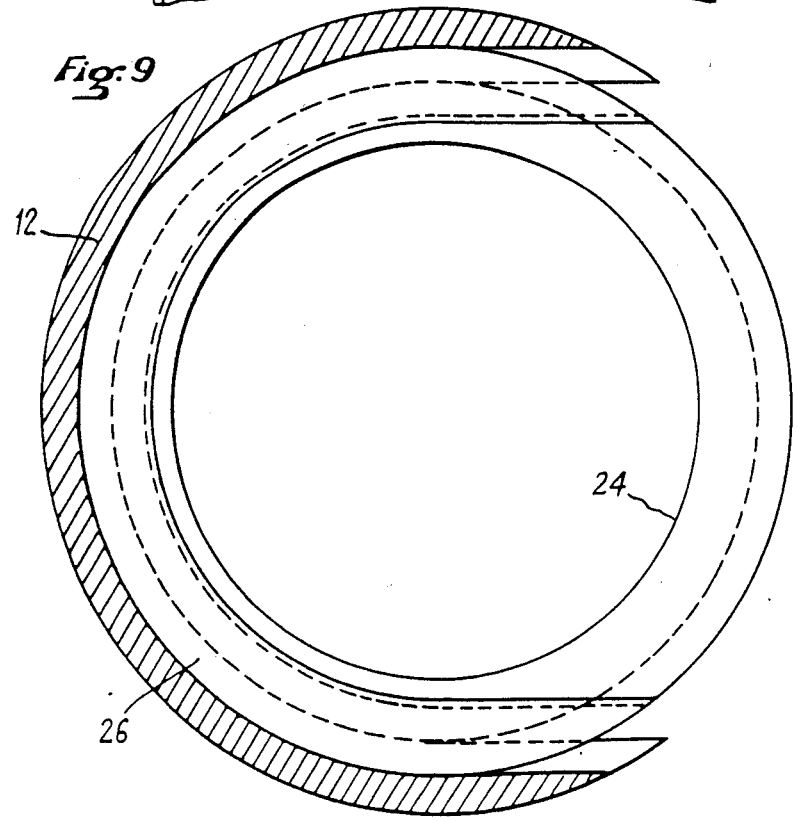
FIG. 9 is a section along plane IX—IX of FIG. 8.

The connectors 6 having been fixed on the arteries and veins 3a and 3b, the blood-filled prosthesis is then placed in position and the different connectors 6 are connected to the corresponding different connectors 2, in the manner indicated hereinabove, by sliding parallel to the plane and to the direction 35 of the extension 32 of each plate 30. The situation shown in FIGS. 6 and 7 is then attained, in which the tubular part 14b of each seal 14 is pushed, by the corresponding plate 30, towards the inside of the connector 6.

From that moment, the surgeon must bleed the cavities defined between the pairs of connectors 2, 6 and the vein and artery clipping devices 4 (cf. also FIG. 10).

The surgeon has the choice between two processes:
(a) either the conventional process employing a syringe, carried out by progressively loosening the devices 4;
(b) or a process which carries out the principle of pumping of the artificial heart 1. To explain this principle, FIG. 10 schematically shows the blood bag 33 of one of the ventricles and a rigid inner membrane 34 separating the two ventricles. Compression of the blood bag 33 is effected by introduction of compressed gas at 35.

Therefore, if this ventricle is placed under light gaseous pressure and if one of the plates is drawn very slightly towards the outside, a communication is established between the heart and the space to be bled so that the blood contained in the heart 1 spurts into this space, without the clipping devices 4 having to be loosened and without risk of air entering the heart.

The level of blood rises slowly in the space to be bled and the pressure of the air occluded therein increases.

Now, the supple bellows 8 made of DACRON are impermeable to blood but permeable to air.

It therefore suffices to maintain the bellows 8 constantly in the highest position for bleeding to be complete.

The advantage of this process over the first is that the blood pressure is much higher and bleeding is more complete and more rapid.

After the bleeding operation, carried out by one or the other of these processes, the surgeon will successively draw each of the four plates 30 with which the heart is fitted, in a quick gesture, by gripping them by their extension 32.

It is seen that, in this way (FIGS. 8 and 9), the locking seal 14 is suddenly released.

It abuts by its tubular part 14b on the bottom of the flat recess 27 and exerts thereon a constant force.

Tightness is therefore immediately and durably ensured without any take-up of air.

Moreover, this seal 14 prevents the return of the connector 6 with respect to the connector 2 by rendering impossible the lateral movement by abutment on the apex of the dove-tail 29. Locking is therefore effected.

However, if an accident were to occur at that moment and it were necessary to disconnect the heart 1 from the four connectors 6, it would suffice to cut the sutures 5 connecting these connectors with the arteries or atria and then to rotate them through 180° to annul the locking effect of the seal 14 and to disconnect the connectors 2.

What is claimed is:
1. In a quick connect system for connecting a blood vessel and a cardiac prosthesis, comprising two cooperating annular connectors, one fixed to said prosthesis and the other adapted to be fixed to the end of said blood vessel;
   a removable obturating plate mounted on said connector fixed to the cardiac prosthesis so as to be able to slide in a plane at least substantially orthogonal to the axis of said connector, said plate comprising an outward extension enabling it to be gripped, when it is in its obturating position;
   said connectors being provided with complementary connecting means enabling them to be joined one to the other, when said plate is in its obturating position, without preventing sliding movement of said plate; and
   said connector to be fixed to said blood vessel being provided with sealing means which, when the connectors are joined one to the other, ensures tightness therebetween, and which maintains said connectors in their joined position, if said plate is separated by a sliding movement from said connector which bears it.
2. The quick connect system of claim 1, wherein said obturating plate is transparent.
3. The quick connect system of claim 1, wherein the removable obturating plate moves parallel to a radial direction of said connector fixed to the cardiac prosthesis
   and said means for complementary connection of said connectors enable the latter to be joined one to the other by a sliding movement in a direction parallel to the radial direction of slide of said plate.
4. The quick connect system of claim 3, wherein the outer part of the connector fixed to the prosthesis forms a flange adapted to be held prisoner between a pair of coaxial, parallel rings borne by the connector adapted to be fixed to said blood vessel,
   and the ring of said pair located towards the outside is open in order to allow said connectors to be joined by sliding.
5. The quick connect system of claim 4, wherein the obturating plate is housed and guided in a flat recess made in the face of said flange directed outwardly, said recess opening out on the periphery of said flange.
6. The quick connect system of claim 5, wherein said sealing means comprises a tubular part coaxial to said rings of the connector to be fixed to said blood vessel and an annular part at right angles to the axis of said tubular part, said annular part being disposed towards the inner face of the inner ring of said pair and being anchored on its periphery on said connector to be fixed to the vessel, whilst said tubular part passes in the central hole of said inner ring to project between said rings, and
   when the connectors are joined one to the other, the free end of said tubular part is applied on said plate if the latter is in its position of obturation or in a position of partial obturation and is applied on the bottom of said flat recess serving as housing for the plate by hooking behind the edge thereof, if said plate is separated from the connector which bears it.
7. The quick connect system of claim 5, wherein the edge of said flat recess and the corresponding edge of said plate are shaped as a dovetail widening inwardly of the connector fixed to the cardiac prosthesis.

* * * * *